United States Patent [19]
Policastro et al.

[11] Patent Number: 5,788,641
[45] Date of Patent: Aug. 4, 1998

[54] DEVICE FOR ESTIMATING CENTRAL VENOUS PRESSURE

[75] Inventors: Dennis C. Policastro, Orchard Park; Robert E. Mates, Buffalo; Kenneth Peebles, Lancaster, all of N.Y.

[73] Assignee: Research Foundation of State University of New York at Buffalo, Amherst, N.Y.

[21] Appl. No.: 951,432

[22] Filed: Oct. 16, 1997

Related U.S. Application Data

[62] Division of Ser. No. 565,444, Nov. 30, 1995.

[51] Int. Cl.$^6$ .......................................... A61B 5/00
[52] U.S. Cl. ...................... 600/485; 600/500; 600/561
[58] Field of Search .......................... 600/485, 486, 600/488, 500, 561

[56] References Cited

U.S. PATENT DOCUMENTS

| | | | |
|---|---|---|---|
| 3,413,970 | 12/1968 | Rockwell | 128/2.05 |
| 3,602,214 | 8/1971 | London et al. | 128/2.05 |
| 4,204,547 | 5/1980 | Allocca | 128/748 |
| 4,348,815 | 9/1982 | Hurt | 33/419 |
| 4,399,616 | 8/1983 | Jansson | 33/161 |
| 4,451,993 | 6/1984 | Yauk | 33/472 |
| 4,452,252 | 6/1984 | Sackner | 128/693 |
| 4,456,015 | 6/1984 | Sackner | 128/721 |
| 4,554,746 | 11/1985 | Echeverria | 33/447 |
| 4,566,462 | 1/1986 | Janssen | 128/677 |
| 4,679,567 | 7/1987 | Hanlon et al. | 600/488 |
| 4,798,588 | 1/1989 | Aillon | 600/486 |
| 4,813,149 | 3/1989 | Herkimer | 33/462 |
| 4,986,277 | 1/1991 | Sackner | 600/485 |
| 5,040,540 | 8/1991 | Sackner | 600/485 |
| 5,280,789 | 1/1994 | Potts | 600/485 |
| 5,353,509 | 10/1994 | Black | 33/451 |
| 5,446,969 | 9/1995 | Terenzoni | 33/419 |

FOREIGN PATENT DOCUMENTS

| | | |
|---|---|---|
| 0 359 972 A1 | 3/1990 | European Pat. Off. |
| 452332 A | 12/1974 | U.S.S.R. |
| 1477377 A1 | 5/1989 | U.S.S.R. |
| WO 92/22871 | 12/1992 | WIPO |

OTHER PUBLICATIONS

Bates, Barbara et al., A Guide to Physical Examination and History Taking, Sixth Edition, 1995, pp. 270–271.
Constant, Jules M.D., Bedside Cardiology, Third Edition, 1985, pp. 80–86.

*Primary Examiner*—Robert L. Nasser
*Attorney, Agent, or Firm*—Kathleen R. Terry; Robert E. Mates

[57] ABSTRACT

A device capable of providing non-invasive, accurate estimates of central venous pressure. This diagnostic device is particularly useful with patients suffering from cardiac disease.

15 Claims, 5 Drawing Sheets

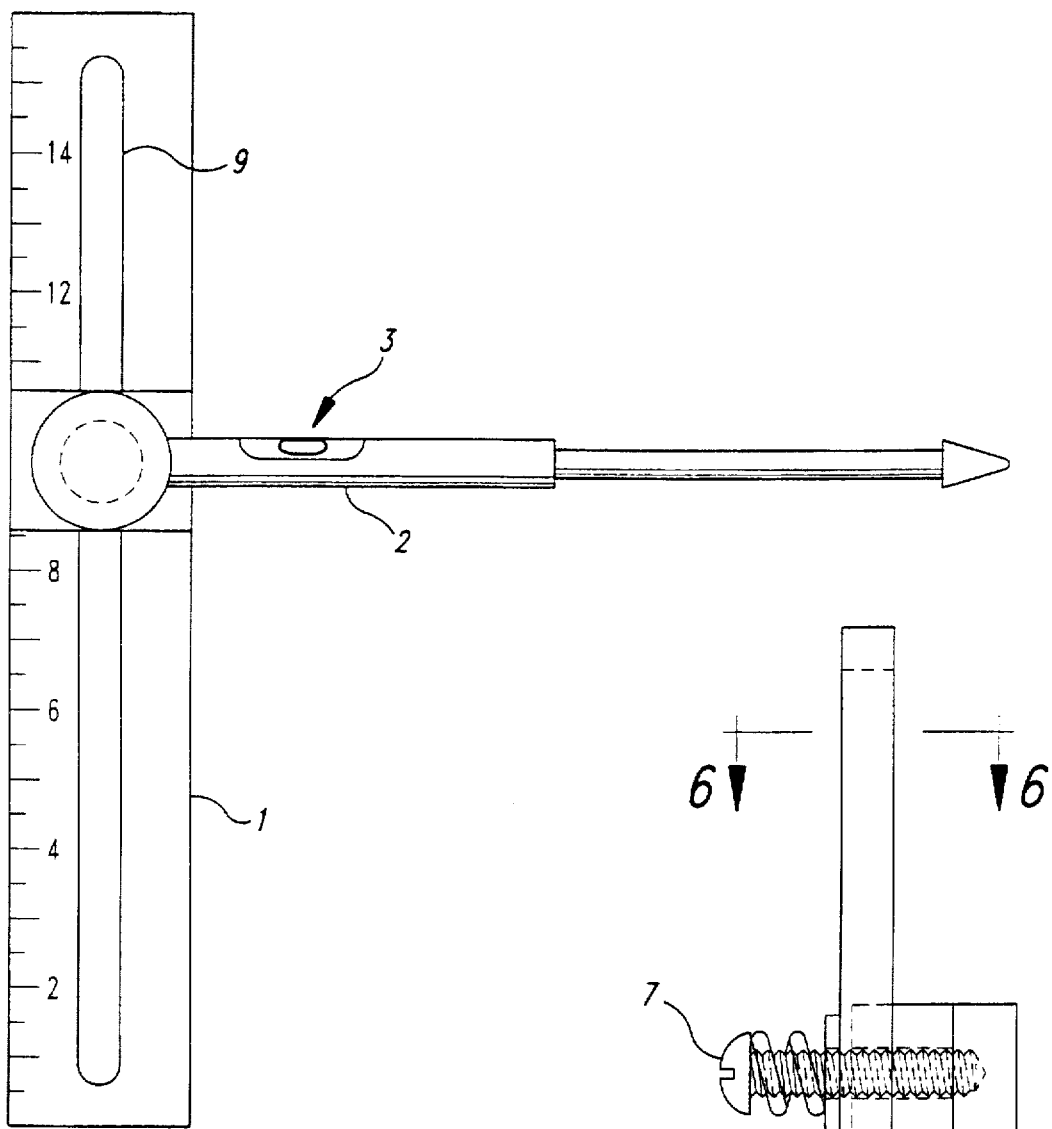

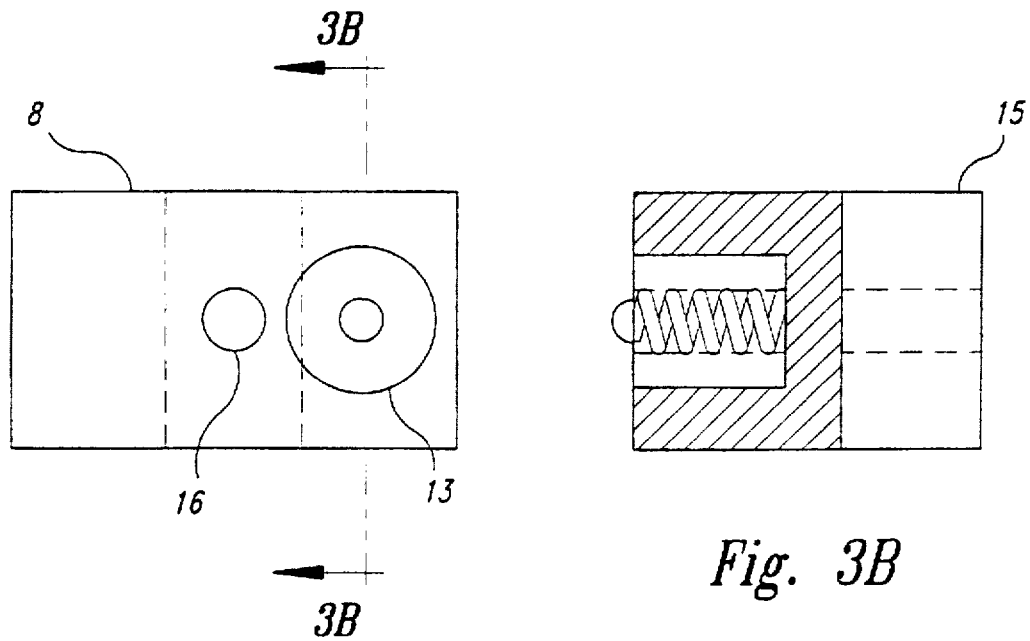
Fig. 3A
Fig. 3B
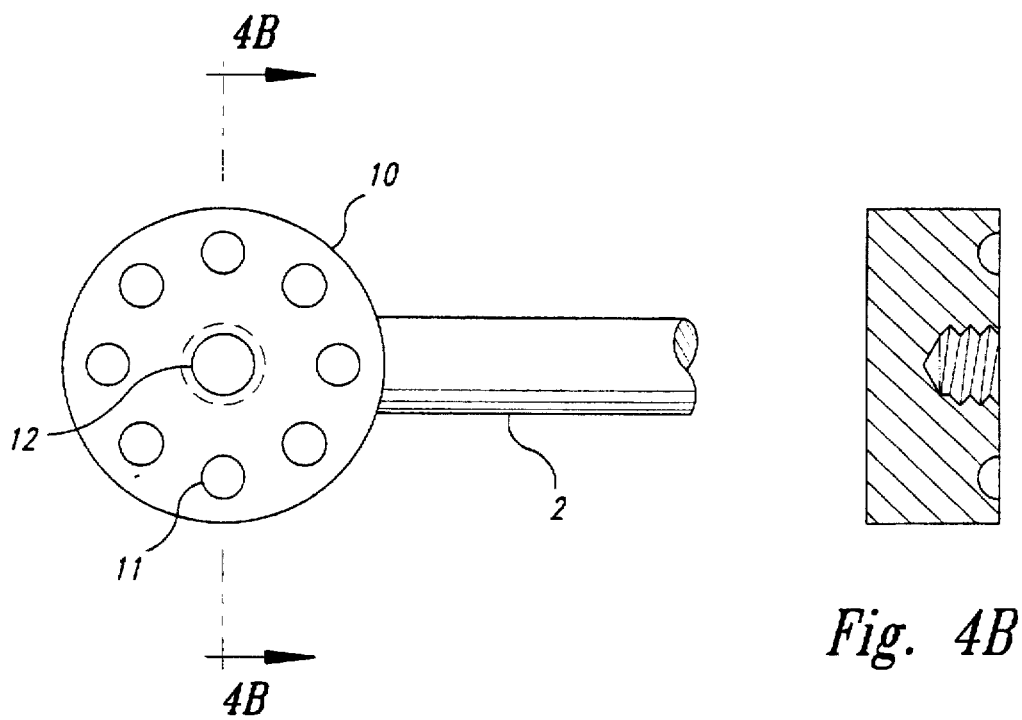
Fig. 4A
Fig. 4B

DEVICE FOR ESTIMATING CENTRAL VENOUS PRESSURE

CROSS-REFERENCE TO RELATED APPLICATION

This application is a division of U.S. patent application Ser. No. 08/565,444, filed Nov. 30, 1995.

BACKGROUND OF THE INVENTION

1. Field of the Invention

The present invention relates to a novel device for estimating central venous pressure.

2. Description of the Related Art

An accurate, quick, and non-invasive means for estimating central venous pressure (hereinafter CVP) is a valuable diagnostic tool for patients suffering from cardiac disease. In a patient suffering from cardiac disease the heart fails to pump sufficient volume through the circulatory system, and this causes blood to "back up" in the veins returning blood to the heart. Excess blood volume which is not pumped through by the heart muscle causes blood pressure in the veins, or venous pressure, to increase which results in distension or expansion of the patient's veins.

A precise measurement of CVP, or the blood pressure in the right atrium of the heart, is often necessary for the diagnosis of a patient with cardiac disease. The most reliable and accurate method of measurement involves the insertion of a catheter into one of the major veins in the circulatory system. The catheter is threaded through the vein until it reaches a position near the heart where a pressure measurement is taken. Such a procedure is invasive, medically risky, and highly traumatic for the patient.

Invasive measures which establish CVP are used only when an accurate measurement is absolutely necessary. Non-invasive methods are used when an estimate of CVP is sufficient for diagnosis. A simple method for estimating CVP is described in B. Bates, L. Bickley & R. Hoekelman, A Guide to Physical Examination and History Taking 270–271 (1995) and in J. Constant, Bedside Cardiology 80–86 (1985). The cited pages are incorporated herein by way of reference.

The physiological basis for the method is that in a healthy individual who is standing or sitting the blood pressure in the internal jugular vein, which is located behind the sternomastoid muscle in the neck, is lower than atmospheric pressure because gravity aids the movement of blood toward the heart. The internal jugular vein in this situation is normally partially collapsed. When blood "backs up" in the veins due to cardiac disease the internal jugular vein expands and pulsations in the vein are visible on the surface of the neck. The visible pulsations begin at the base of the neck and progress upward as CVP increases. A measurement of the height of the highest location on the neck where pulsations are visible provides a simple and non-invasive method for estimating CVP. The internal jugular vein is thereby used as a manometer to estimate CVP.

The above-mentioned procedure comprised the following steps: the head of the patient's bed is placed at an elevated angle, pulsations in the internal jugular vein are located, and the highest point at which these pulsations are visible is measured. Conventionally, the height of this point is measured from the sternal angle, also called the angle of Louis, which is a reference point on the sternum. The sternal angle is roughly 5 centimeters above the right atrium. The height measurement is taken by placing the base of a centimeter ruler on the sternal angle while the ruler is held in a vertical orientation. A tongue depressor or other straight object is then placed at a right angle with respect to the ruler and is used to locate the highest visible pulsations. A physician may also merely estimate the height visually. If the highest visible pulsations are more than a specified number of centimeters above the sternal angle then the CVP is considered elevated. A diagram indicating this method is shown in FIG. 5.

Several other methods or devices may be used to estimate CVP. Rockwell, in U.S. Pat. No. 3,413,970, discloses an integral, one piece arm which supports a slidable member. The slidable member is extended to a prescribed position under a patient to establish the vertical position of the patient's superior vena cava, after which a scale on the arm may be used to set a baseline for a manometer. The arm includes a level indicating means afixed thereto. The CVP measurement is invasive. Sackner, in U.S. Pat. Nos. 4,452, 252, 4,456,015, 4,986,277, and 5,040,540, discloses several transducers which are wrapped around a patient's neck to measure changes in the cross-sectional area of the neck. Those changes are related to CVP. Allocca, in U.S. Pat. No. 4,204,547, discloses a method of monitoring intracranial pressure by occluding the jugular vein at a particular point and measuring the rate of change of blood pressure upstream of that point. Soviet Patent No. SU-452332-A discloses the measurement of venous pressure while the patient's inclined position is raised.

The need remains for an accurate and non-invasive method for estimating central venous pressure.

SUMMARY OF THE INVENTION

The object of this invention is to provide a device which enables an accurate and non-invasive estimation of central venous pressure. A device according to the invention is comprised of a substantially straight bar having a bottom portion and a top portion. A graduated scale is afixed to or etched into the surface of the bar beginning approximately at the bottom portion. A pointer comprising a pivoting base, a telescoping member and a distal end is movably attached to said bar at its pivoting end such that the pointer slides along the length of the bar. The pointer further comprises a bubble-type indicator means formed integrally therewith. The distal end of the pointer extends in a straight manner from the bar and is extended by the telescoping member. The pointer is rotatable with respect to the bar such that the angle between the bar and the pointer is adjustable. Detents in the pivoting base fix and hold the pointer at several preset angles.

BRIEF DESCRIPTION OF THE DRAWINGS

FIG. 2 illustrates a front view and a side view of the device;

FIG. 3 illustrates two views of the detent bracket;

FIG. 4 illustrates two views of the pivoting base of the pointer;

DESCRIPTION OF THE PREFERRED EMBODIMENT

Figure 1:
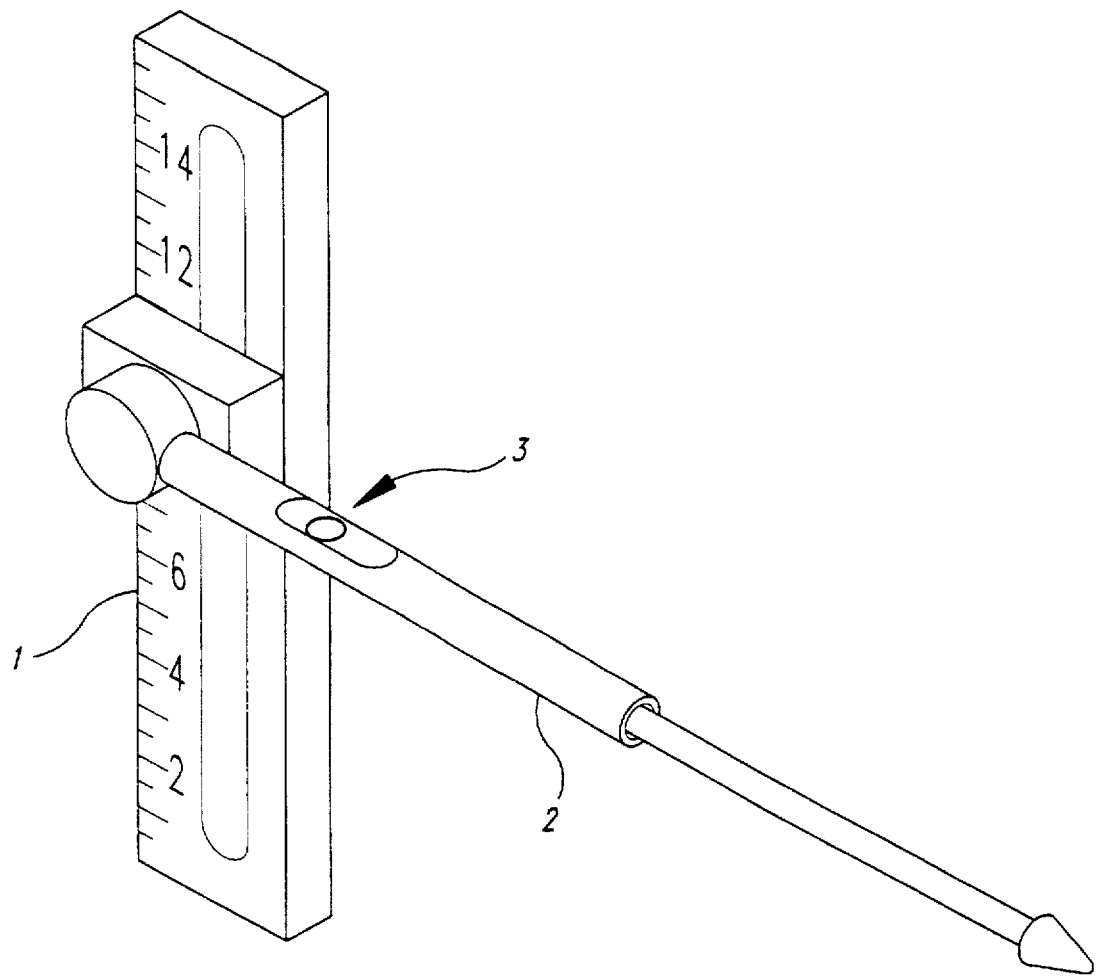
FIG. 1 illustrates a perspective view of the device.
Figure 5:
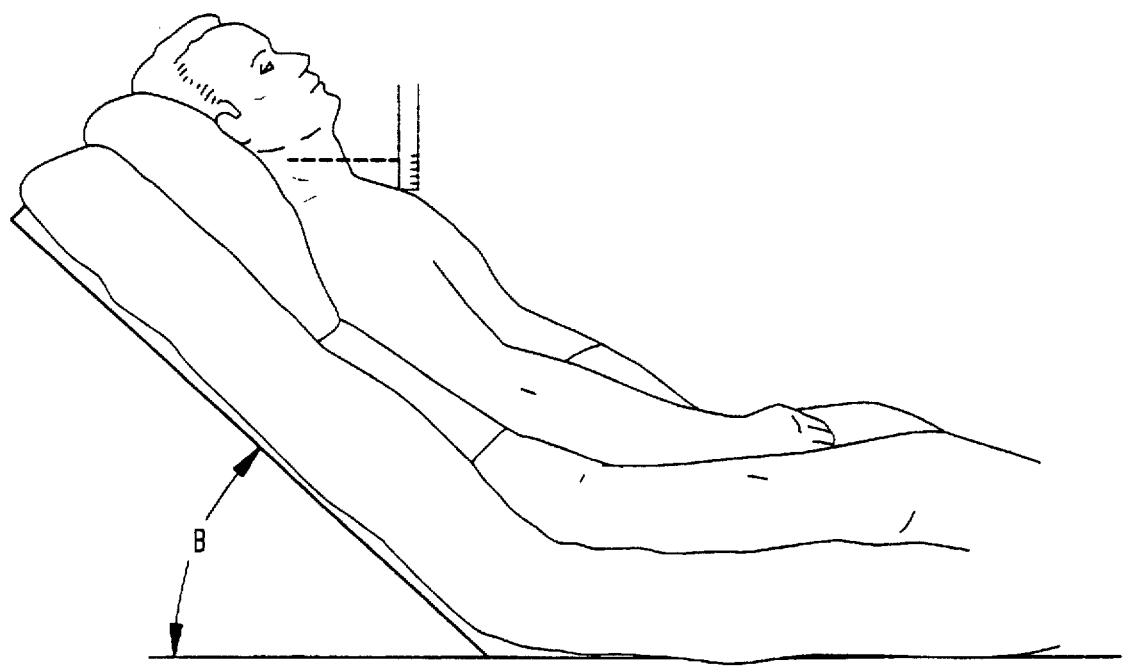
FIG. 5 illustrates the conventional method of estimating central venous pressure in a non-invasive manner.

A perspective view of a device according to the invention is shown in FIG. 1. A substantially straight bar 1 supports a telescoping pointer 2 which is rotatably attached to the bar. Bubble-type indicating means 3 is integrally formed within the telescoping pointer.

FIG. 2 shows a front view and a side view of the device. Bar 1 has a slot 9 integrally formed therein, and a graduated scale in centimeters is etched or otherwise permanently affixed to an edge of bar 1. The graduated scale begins at a bottom portion of the bar and increases along the length of the bar toward a top portion.

Pointer 2 is shown in FIG. 1 and FIG. 2 and is comprised of a telescoping member with a distal end, a pivoting base 10, and bubble-type indicating means 3 formed integrally therewith. The bubble-type indicating means indicates when the pointer 2 is in a horizontal position. The telescoping distal portion is comprised of a plurality of interfitting cylinders of progressively decreasing diameter, wherein each adjacent cylinder fits inside the preceding cylinder. The last cylinder extends furthest from the pivoting base and is formed with a blunt cap on the furthest distal end.

Pivoting base 10 shown in FIG. 4 has a threaded hole 12 in the center thereof and a plurality of circular depressions 11 spaced equidistantly from the center hole 12 along a circular centerline. The depressions face detent bracket 8 which is slidably positioned in slot 9, shown in FIG. 2. The detent bracket, detailed in FIG. 3, is integrally formed with rudder 15 which intersects slot 9 in slidable fashion such that the detent bracket may slide along the length of bar 1. Detent 13 is formed inside the detent bracket and is comprised of a hole inside the bracket in which a spring is set which forces a ball bearing toward the surface of the detent bracket such that the ball bearing protrudes slightly through the surface of the bracket. When pressure is exerted on the ball bearing against the force of the spring the ball bearing recedes below the surface of the bracket. The ball bearing returns to protrude from the surface when said pressure is released. Detent 13 faces depressions 11 when pivoting base 10 is held against detent bracket 8 as shown in FIG. 2.

Figure 6:
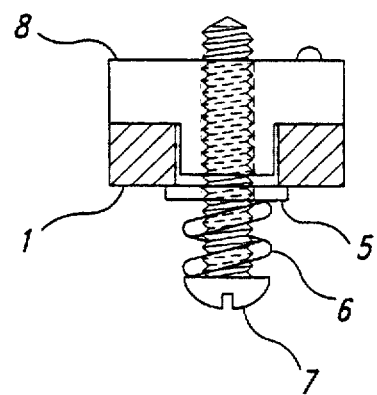
FIG. 6 illustrates a sectional view of the bar and detent bracket.
Figure 7:
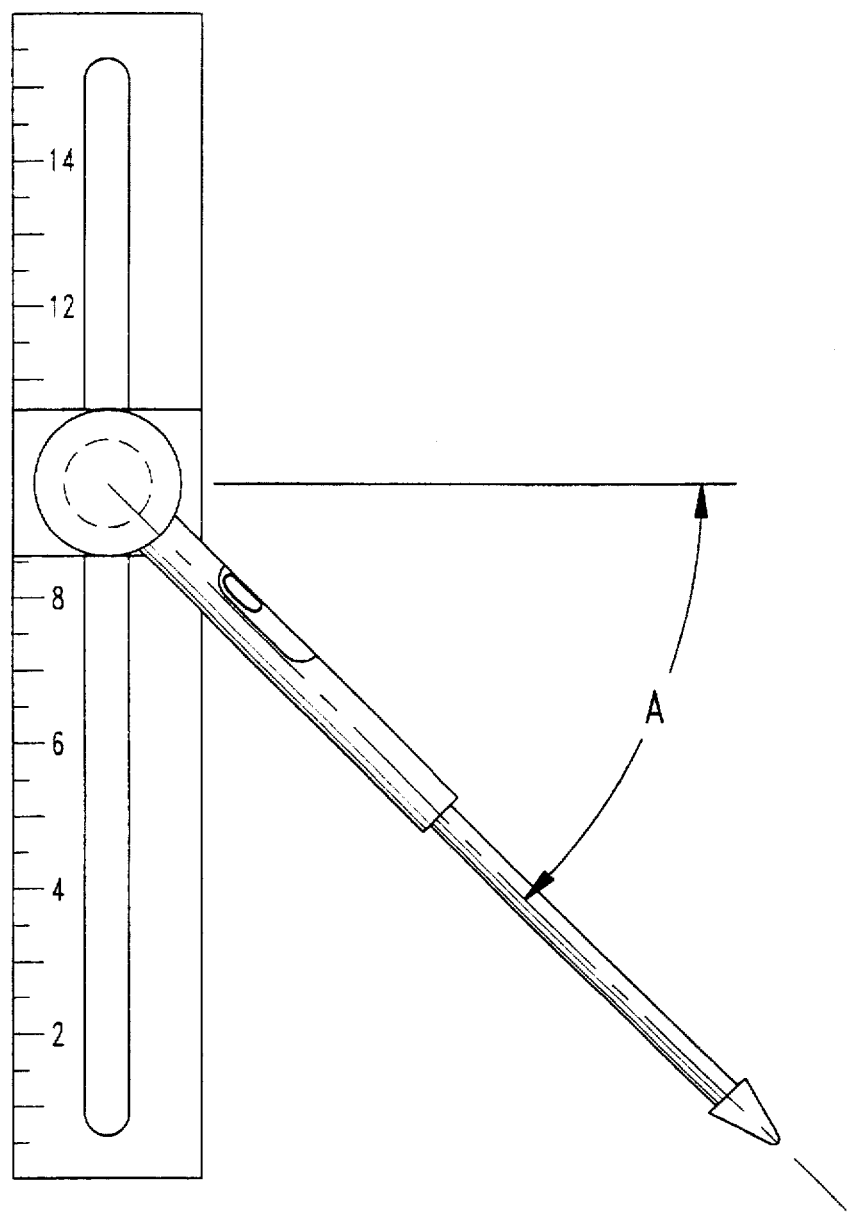
FIG. 7 illustrates a front view of the device with the telescoping pointer at an angle.

The detent bracket 8 and the base 10 are urged against each other by retaining screw 7 which is slidably received both in slot 9 and in hole 16 of bracket 8 and fixedly received in threaded hole 12 of pivoting base 10. As shown in FIG. 6 the retaining screw head is held in place by spring 6 and washer 5 on the side of the bar opposite that on which pivoting base 10 is located. Spring 6 biases the retaining screw head away from bar 1 such that pivoting base 10 and detent bracket 8 are held against bar 1 in a rigid fashion. Detent 13 intersects with one of depressions 11 to rigidly maintain the pivoting base and pointer 2 at a prescribed angle with respect to bar 1. The positioning of depressions 11 define where the detent will engage and therefore the angles at which pointer 2 may be held. Detent bracket 8 and pivoting base 10 together may be pushed along the length of the slot to adjust the height of the pointer. The force of spring 6 holds this assembly in its final position. Detent 13 may be disengaged from pivoting base 10 by pulling the pivoting base outward such that spring 6 is compressed. The pivoting base may be rotated about the axis of retaining screw 7 until the desired angle is reached at which point the pivoting base is released allowing spring 6 to force the rigid engagement of detent 13 and one of depressions 11.

To use the device, a physician first places the pointer at an angle, typically 45 degrees with respect to the bar, and the bar is placed parallel to the frame of a bed. The head of the bed is adjusted until the bubble-type indicating means indicates that the pointer is horizontal and the head of the bed is elevated at a 45 degree angle. Next, the pointer is placed at a 90 degree angle with respect to the bar by engaging the detent at the 90 degree recess and the bottom portion of the bar is positioned on the sternal angle such that the bubble-type indicating means indicates that the pointer is horizontal and the bar is vertical.

This is the critical step in the procedure in that an accurate estimate of the height of visible pulsations is based on the bar being in a vertical orientation and the pointer being in a horizontal orientation. The bubble-type indicating means enables the user to fix the pointer along a true horizontal and the 90 degree detent rigidly holds the pointer at a 90 degree angle with respect to the bar.

The telescoping distal end of the pointer is then extended to a position close to the patient's neck and the height of the pointer is adjusted by sliding the pivoting base along the length of the graduated bar. The distance between the sternal angle and the height of highest visible pulsations in the internal jugular vein is then gauged according to the graduated scale. The device enables a more accurate and repeatable estimation of central venous pressure in a non-invasive, risk-free manner, resulting in improved patient care.

The device is intended for external, non-invasive use only and should not come in contact with bodily fluids during the above-described procedure. For that reason the device may be used repeatedly without need of sterilization. Should the device come into contact with any form of contaminant a simple alcohol wash or other sterilization method would allow the immediate reuse of the device.

The device may be constructed of any rigid material which can withstand the stresses of the above-described procedure and maintain structural integrity to enable accurate estimations of central venous pressure. The device material should also be able to withstand a simple alcohol wash or other sterilization procedure. For example, the bar, the base, and the detent bracket may be made of rigid plastic. The interfitting cylinders of the pointer may be comprised of metal. Those skilled in the art will recognize many other materials which would meet the structural and durability requirements of the device.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

For example, the depressions 11 fixing the angle at which the telescoping pointer may be oriented with respect to the base can be set at various intervals. The method of estimating CVP described above may take place while the upper torso of the patient is at any substantial angle with respect the the horizontal. Dr. Bates, in *A Guide to Physical Examination and History Taking*, indicates that the measurement may be taken with the patient elevated at an angle of fifteen degrees or more. The depressions may therefore be set at fifteen, thirty, forty-five, sixty, and ninety degrees or any combination thereof, or in any combination of angles between these such that the device is most useful as a diagnostic tool.

In other embodiments within the scope of the invention the mechanical means for linking the telescoping pointer to the bar may be comprised in various ways such that the pivoting base of the pointer is movable along the length of the bar and such that the pointer may be set at various angles with respect to the bar. For example, there may be an indentation rather than a slot in the bar such that the pivoting base of said pointer clamps onto the bar and is movable along the length of the bar.

The vertical measurement along the graduated scale affixed to the bar may be aided by an electronic sensor indicating the height of the pointer with respect to the bottom portion of the bar.

What is claimed is:

1. A method for estimating central venous pressure in a human patient having a neck, an internal jugular vein in the neck, and a chest, the method comprising elevating the neck of the patient;

placing an apparatus for estimating central venous pressure on a reference point on the chest, wherein the apparatus comprises:

an elongated bar having a longitudinal axis and a bottom portion on the longitudinal axis, a pointer comprising an elongated base member having a longitudinal axis and an elongated end member having a longitudinal axis, the base member being movably mounted to the bar and the end member being supported for selected movement along a path substantially parallel to the base member longitudinal axis, and a horizontal indicator mounted on the pointer;

positioning the base member longitudinal axis at a ninety degree angle with respect to the bar longitudinal axis;

placing the pointer in a horizontal attitude indicated by the horizontal indicator;

positioning the bottom portion of the bar on the reference point;

identifying a point of highest visible pulsations in the internal jugular vein;

extending the end member from the base member and moving the pointer relative to the bar such that a distal end of the end member is proximate to the point of highest visible pulsations in the internal jugular vein;

measuring a vertical distance between the reference point and an intersection of the pointer and the bar to estimate the central venous pressure.

2. The methods of claim 1 wherein the step of positioning the bottom portion of the bar comprises positioning the bottom portion of the bar on a sternal angle of the chest.

3. A method for estimation central venous pressure in a human patient having a neck, and internal jugular vein in the neck, and a chest, the method comprising:

elevating the neck of the patient above the chest;

providing an apparatus having an elongated bar with a longitudinal axis and a bottom portion and an extendable pointer translatably mounted to the bar;

placing the apparatus on a reference point on the chest of the patient;

positioning a longitudinal axis of the pointer at a ninety degree angle with respect to the bar longitudinal axis;

placing said pointer in a horizontal attitude;

identifying a point of highest visible pulsations in the internal jugular vein;

positioning the bottom portion of the bar on the reference point;

extending the pointer such that a distal end of the pointer is proximate to the neck;

moving the pointer relative to the bar to a position such that the distal end is proximate to the point of highest visible pulsations in the internal jugular vein;

measuring a vertical distance between the reference point and a position of the pointer along the longitudinal axis of the bar to estimate central venous pressure.

4. The method of claim 3 wherein the step of positioning the bottom portion comprises positioning the bottom portion of the bar on a sternal angle on the chest.

5. A method for estimating central venous pressure in a human patient having a neck, an internal jugular vein in the neck, and a chest having a sternal angle, the method comprising;

providing a device having an elongated bar with a longitudinal axis and a bottom portion, the bar having a first cross-sectional area in a plane perpendicular to its longitudinal axis, the bottom portion being on the bar longitudinal axis, the device including a pointer having an elongated base member with a longitudinal axis and an elongated end member with a longitudinal axis, the end member having a second cross-sectional area in a plane perpendicular to its longitudinal axis which is less than the first cross-sectional area, the base member being mounted to the bar, the end member being supported by the base member and being extendible from a retracted position to an extended position substantially parallel to the base member longitudinal axis, the device also including a level indicator mounted on the pointer, the level indicator being structured to indicate when the pointer is in a horizontal attitude;

situating the patient in a reclining position such that the neck is elevated from the sternal angle;

positioning the bottom portion of the bar proximate to the sternal angle, observing a point of highest visible pulsations in the internal jugular vein;

positioning the pointer in a horizontal attitude;

extending the end member to a location proximate to the neck;

moving the base member with respect to the bar to a position such that the end member is proximate to the point of highest visible pulsations in the internal jugular vein; and gauging a distance along the bar longitudinal axis between the sternal angle and the pointer to estimate the central venous pressure.

6. The method of claim 5 wherein the step of positioning the pointer in a horizontal attitude comprises:

positioning the base member longitudinal axis at a ninety degree angle with respect to the bar longitudinal axis; and positioning the bar such that the level indicator indicates that the pointer is in a horizontal attitude.

7. The method of claim 6 wherein the step of extending the end member comprises extending the end member substantially parallel to the base member longitudinal axis to a position such that a distal end of the end member is proximate to the neck.

8. The method of claim 7 wherein the step of moving the base member comprises sliding the base member along the bar longitudinal axis until the distal end of the end member is proximate to the point of highest visible pulsations in the internal jugular vein.

9. The method of claim 8 wherein the step of gauging a distance further comprises reading a graduated scale between the bottom portion of the bar and an intersection between the base member and the bar.

10. A method for estimating central venous pressure in a human patient having a neck, an internal jugular vein in the neck, and a chest, the method comprising:

elevating the neck above the chest;

locating a bottom portion of an elongated bar at a selected location on the chest;

positioning an elongated pointer translatably mounted to the bar in a horizontal attitude and at a right angle with respect to a longitudinal axis of the bar;

observing a point of highest visible pulsations in the internal jugular vein;

extending the pointer to a location proximate to the neck;

moving the pointer relative to the bar so that the pointer is proximate to the point of highest visible pulsations in the internal jugular vein; and gauging a distance between the selected location on the chest and an intersection between the pointer and the bar to estimate the central venous pressure of the patient.

11. The method of claim 10 wherein the step of locating a bottom portion of an elongated bar comprises locating a bottom portion of an elongated bar proximate to a sternal angle of the patient.

12. The method of claim 11 wherein the step of positioning an elongated pointer comprises:

positioning a longitudinal axis of the pointer at a ninety degree angle with respect to the bar longitudinal axis; and positioning the bar such that a level indicator mounted on the pointer indicates that the pointer is in a horizontal attitude.

13. The method of claim 12 wherein the step of extending the pointer comprises extending an elongated end member of the pointer substantially parallel to the pointer longitudinal axis to a position such that a distal end of the end member is proximate to the neck.

14. The method of claim 13 wherein the step of moving the pointer comprises moving the pointer relative to the bar such that the distal end of the end member is proximate to the point of highest visible pulsations in the internal jugular vein.

15. The method of claim 11 wherein the step of estimating a distance comprises estimating a vertical distance along the bar longitudinal axis between the sternal angle and an intersection between the pointer and the bar.

* * * * *